United States Patent [19]

Nakajima

[11] Patent Number: 5,200,559
[45] Date of Patent: Apr. 6, 1993

[54] PROCESS FOR PRODUCING SORBIC ACID

[75] Inventor: Masahiro Nakajima, Minamatashi, Japan

[73] Assignee: Chisso Corporation, Osaka, Japan

[21] Appl. No.: 760,196

[22] Filed: Sep. 16, 1991

[30] Foreign Application Priority Data

Oct. 15, 1990 [JP] Japan .................................. 2-275756

[51] Int. Cl.$^5$ ...................... C07B 35/04; C07C 57/10
[52] U.S. Cl. .................................... 562/599; 562/601
[58] Field of Search ................................. 562/599, 601

[56] References Cited

U.S. PATENT DOCUMENTS 3,865,872  2/1975  Fernholz ............................. 562/601
3,960,939  6/1976  Sekiyama ........................... 562/601

Primary Examiner—José G. Dees
Assistant Examiner—Joseph M. Conrad, III
Attorney, Agent, or Firm—Fred Philpitt

[57] ABSTRACT

A process for producing sorbic acid from a polyester obtained by reaction of crotonaldehyde with ketene using an organic acid zinc salt as catalyst is provided, which process comprises dissolving the polyester in an aromatic hydrocarbon solvent having an azeotropic temperature of the solvent with water of 92° to 100° C., followed by washing the polyester solution with water or a mineral acid water to remove zinc matter and continuously contacting the solution with a strongly acidic porous ion exchange resin, the process being simple, commercially profitable, making possible a long term operation of the polyester decomposition apparatus, capable of easily purifying sorbic acid and affording sorbic acid with a good yeild.

2 Claims, No Drawings

PROCESS FOR PRODUCING SORBIC ACID

BACKGROUND OF THE INVENTION

1. Field of the Invention

This invention relates to a process for producing sorbic acid. More particularly, it relates to a process for sorbic acid commercially and advantageously, from a polyester obtained from the reaction of crotonaldehyde with ketene (hereinafter referred to merely as polyester).

2. Description of the Related Art

Sorbic acid or its salts either have superior fungiresistance; hence they have been preferably used as a food preservative.

The process for producing sorbic acid includes those of reacting crotonaldehyde with ketene to obtain a polyester via $\beta$-lactone as an intermediate, followed by subjecting the polyester to acidolysis, thermal decomposition or alkaline decomposition to produce sorbic acid, and among these processes, acidolysis process has generally been often carried out.

As the acidolysis process, a mineral acidolysis process using a mineral acid such as hydrochloric acid or sulfuric acid as a catalyst, a decomposition process with an ion exchange resin using as a catalyst, an acidic giant reticulated ion exchange resin (MR) having pores of at least 200 Å on an average and a water content of 20% by weight or less (Japanese patent publication No. Sho 57-47,655), or the like processes are known.

According to the mineral acidolysis process, there are advantages that the polyester is not only decomposed into sorbic acid, but also a byproduced cis-isomer is isomerized into sorbic acid, but a problem is raised that a black-brown byproduct is formed simultaneously with the polyester decomposition, whereby crystals of sorbic acid are contaminated to make their purification difficult. Further, an additional problem is raised that catalyst-mineral acid water is contaminated to make its circulation use difficult; hence the mineral acidolysis process cannot always be regarded as a commercially advantageous production process.

On the other hand, the decomposition process with an ion exchange resin is superior to the mineral acidolysis process in that the quantity of the black-color byproduct formed is very small, but the present inventors found as a result of the tracing test of the former process, a problem that the ion exchange resin loses its catalytic activity within such an unexpectedly short time that the catalyst cannot be practically used.

In order to solve the above problem, we attempted to restore the catalytic acitivity by adding a mineral acid, as carried out in the prior art, but the restoring effect was small and to the contrary, various new problems occurred such as a problem of formation of a balck-brown byproduct due to the mineral acid, a problem of corrosion of equipment, and a problem that since the added mineral acid mixes in crystals of sorbic acid, it is necessary to remove the acid. The decomposition process with an ion exchange resin has a problem in that it is difficult to control the water content of the ion exchange resin used.

Namely, in general, ion exchange resins have been commercially availed in a hydrous state of a water content in the vicinity of 50%, and when the water contained in the ion exchange resins is removed by means of azeotropic distillation, etc. as much as possible, in order to enhance the catalytic acitivity, then the catalytic activity is entirely lost, while when the water content is increased to the contrary, the catalytic activity is lost after a certain time. Thus, the subject to be solved by the invention is to provide a more advanced process for producing sorbic acid, having overcome the above-mentioned problems.

The present inventors have examined the reduction in the catalytic activity as one of the above problems in the case of the decomposition process with an ion exchange resin, and as a result have found that the reduction is deeply related to impurities contained in the polyester, particularly to zinc, that is, when the polyester is prepared from crotonaldehyde and ketene, an ion exchange occurs between a zinc salt and the exchange group of the exchange resin to reduce the acid concentration of the ion exchange resin and thereby lose the catalytic function of the resin and as a result, reduce the percentage of decomposition of the polyester into sorbic acid.

In order to recover the lost catalytic function of the ion exchange resin, it is necessary to wash the resin with about 5 to 10% hydrochloric acid, sulfuric acid or the like to dissolve away zinc, but as a result, since the ion exchange resin contains a large quantity of water, a cumbersome matter occurs that the resin should be dehydrated up to an adequate water content.

Thus, the present inventors have made extensive research in order to find a process of not damaging the catalytic life of the ion exchange resin, and as a result have found that when the polyester is first dissolved in a solvent, followed by washing the resulting solution with a mineral acid water and, if the zinc salt is water-soluble, washing it with water in advance, the object can be easily achieved.

Next, the present inventors have made extensive research into the catalytic acitivity of the ion exchange resin, and as a result, have found that when the ion exchange resin is treated with, preferably washed with a lower alkyl alcohol to replace a portion of water by the lower alkyl alcohol, the object can be easily achieved without the above difficult control of the water content.

Namely, the ion exchange resin retaining a lower alkyl alcohol in the pores of the resin has a superior affinity to the solution of the polyester dissolved in the solvent, as compared with the ion exchange resin retaining water in the pores of the resin; hence the former resin easily contacts with the solution of the polyester dissolved in the solvent so that decomposition of the polyester raises no obstacle.

This washing process with a lower alkyl alcohol removes alcohol-soluble impurities present in the ion exchange resin, and at the same time the process is applicable to a process for regenerating the ion exchange resin in the case where impurities such as ketene polymer, crotonaldehyde polymer, etc. remaining in the polyester adhere to the ion exchange resin during decomposition of the polyester to reduce the catalytic activity. The present inventors have solved these problems and have completed the present invention.

SUMMARY OF THE INVENTION

As apparent from the foregoing, an object of the present invention is to provide a novel, improved process for producing sorbic acid by decomposing a polyester with an ion exchange resin. Another object of the present invention is to provide an ion exchange resin catalyst for the polyester decomposition, treated with a lower alkyl alcohol, and a process for regenerating the catalyst.

The present invention has the following constitutions (1) to (5):

(1) In the process for producing sorbic acid by decomposing a polyester obtained by reacting crotonaldehyde with ketene in the presence of an organic acid zinc salt, the improvement which comprises dissolving said polyester in an aromatic hydrocarbon solvent having an azeotropic temperature thereof with water of 92° to 100° C., followed by washing the resulting polyester solution with water or a mineral acid water to remove the zinc matter contained therein, and continuously contacting the resulting solution with a strongly acidic porous type ion exchange resin.

(2) The improvement according to item (1), wherein said strongly acidic porous type ion exchange resin is treated with a lower alkyl alcohol in advance, followed by continuously contacting said polyester solution with the treated resin at 60° to 95° C.

(3) The improvement according to item (2), wherein said lower alkyl alcohol is at least one member selected from the group consisting of methanol, ethanol, propanol and isopropanol.

(4) A catalyst for decomposing a polyester obtained by the reaction of crotonaldehyde with ketene in the presence of an organic acid zinc salt, which catalyst comprises a strongly acidic porous type ion exchange resin treated with a lower alkyl alcohol to replace a portion or the total of water contained in said resin by said lower alkyl alcohol.

(5) A catalyst according to item (4), wherein said lower alkyl alcohol is at least one member selected from the group consisting of methanol, ethanol, propanol and isopropanol.

DETAILED DESCRIPTION OF PREFERRED EMBODIMENTS

The constitutions of the present invention will be described in more detail.

Polyester:

The polyester used in the present invention is first prepared by reacting crotonaldehyde with ketene in the presence of an organic acid zinc salt catalyst, followed by heating the resulting polyester under reduced pressure to distil off low boiling matters of crotonaldehyde, a solvent used for the reaction of crotonaldehyde with ketene, diketene, etc. The resulting polyester is used in the present invention.

Dissolution of the polyester:

As the solvent for dissolving the polyester, water-insoluble aromatic solvents which dissolve the polyester in an optional proportion and have an azeotropic temperature thereof with water of 92° to 100° C. are used. Examples of such solvents are xylene, ethylbenzene, mesitylene, etc.

Use of benzene or toluene has no inconvenience upon dissolution of the polyester, but when the polyester is decomposed at 85° to 90° C., such solvents form an azeotrope with water; hence in the system wherein an ion exchange resin is filled in a column and the polyester is decomposed into sorbic acid by passing it through the filled resin layer, the operation is impossible unless a countermeasure such as pressurizing is applied.

Further, in the case of a solvent which forms no azeotrope with water and has a boiling point of 100° C. or higher, when sorbic acid is purified, the cost of removing the solvent attached to sorbic acid is so high that use of such a solvent is undesirable.

The proportion of the polyester to the solvent depends upon the solubility of sorbic acid in the solvent, and a proportion of 3 to 8 parts by weight of the solvent per one part by weight of the polyester is usually employed.

Purification of the polyester:

Purification of the polyester solution depends upon the physical properties of the organic acid zinc salt as the catalyst at the time of preparation of the polyester, and in general, the purification is carried out sufficiently contacting the solution with a mineral acid water to convert the zinc salt into a water-soluble salt or precipitate and separating and removing them.

Thus, in the case of a water-soluble salt such as zinc acetate, even when a mineral acid is not particularly used, it is possible to separate and remove the zinc salt into aqueous layer only by extraction with water.

The acid concentration in the mineral acid water is generally 1% or higher, preferably 5% or higher. Further, even when the concentration of the mineral acid water is elevated, the purification effect is not particularly increased; hence the concentration is preferably 50% or lower in the case of sulfuric acid water or phosphoric acid water and preferably 15% or lower in the case of hydrochloric acid.

Ion exchange resin:

As to the ion exchange resin used in the present invention, among styrene-divinylbenzene system sulfonated strongly acidic porous type resins, resins having an affinity to non-polar solvents are preferably used. Resins having no affinity to non-polar solvents have almost no catalytic function.

Such resins having an affinity to non-polar solvents have been commercially availed in Japan genrally in a hydrous state in the tradenames of Highporous resin (made by Mitsubishi Kasei Co., Ltd.), MP resin (made by Organo Co., Ltd., Sumitomo Kagaku Co., Ltd.), etc.

Such ion exchange resins are filled in a column and used, and when the polyester is decomposed, the ion exchange resins filled in the column together with water or a lower alkyl alcohol are continuously treated i.e. washed by passing the lower alkyl alcohol therethrough, followed by successively washing with the solvent used for dissolving the polyester and using the resulting resin. Such washing conditions (temperature, time) are not particularly limited, but they are usually 10° to 80° C., preferably room temperature, and 10 minutes to 10 hours, preferably 4 to 5 hours. As the lower alkyl alcohol, lower alkyl alcohols such as methanol, ethanol, propanol, isopropanol, etc. are usable.

According to this process, it is unnecessary to use anhydrous lower alkyl alochol in order to make the water content in the ion exchange resin as low as possible, but 0.5 to 5% hydrous commercially available product is usable.

The quantity of the lower alkyl alcohol used for the washing has no particular limitation, but usually, these ion exchange resins contain impurities soluble in the lower alkyl alcohol and the solvent and often make the subsequent purification of sorbic acid difficult; thus the washing is carried out regarding as a measure, that any colored substance dissolved out of the resins is not seen.

Further, an ion exchange resin commercially availed as a dried product may also be alike treated and used.

The alcohol containing water in the thus obtained ion exchange resin may be purified by distillation and reused by circulation.

Decomposition of polyester:

The decomposition of polyester is carried out preferably according to a continuous system of passing a polyester dissolved in an aromatic organic solvent through an ion exchange resin layer filled in a column. The decomposition is possible even by way of an agitation vessel system, but since breakage of the ion exchange resin may occur, such a system is undesirable as an industrial method.

The temperature of the column layer in the case of the polyester decomposition according to the continuous system is set within a relatively narrow temperature range of 60° to 95° C., preferably 65° to 90° C.

If the decomposition temperature is set to the azeotropic temperature of water and a solvent or higher, the water and solvent remaining in the resin forms an azeotrope to make a stabilized operation difficult, and also in the case where water is lost from the ion exchange resin due to the formation of the azeotrope, a serious state of losing its catalytic function occurs. On the other hand, if the temperature is 55° C. or lower, the decomposition speed is too low; hence such temperatures are practically undesirable.

The ion exchange resin catalyst having been reduced in the activity at the time of its use is regenerated according to a process of washing it with a lower alkyl alcohol same as that described in the above item of ion exchange resin. The solution obtained by passing through the column and decomposing the polyester into sorbic acid, is subjected to solid-liquid separation to obtain crystals of sorbic acid.

The solvent in the filtrate is circulated as it is and used for dissolving the polyester.

Effectiveness of the Invention

According to the process of the present invention, a long term operation of a polyester decomposition apparatus becomes possible and sorbic acid capable of being easily purified is obtained with a high yield, by way of a simple process of choice of solvent, preferably use of the polyester and treatment of an ion exchange resin with a lower alkyl alcohol.

The present invention will be described in more detail by way of Examples, but it should not be construed to be limited thereto.

EXAMPLE 1

A hydrous ion exchange resin (RCP-150, tradename of product made by Mitsubishi Kasei Co., Ltd.) was dispersed in hot water at 80° C., followed by filling it into four stainless columns (diameter: 5 cm), each equipped with a jacket and in a resin layer height of 200 cm, washing off a brown eluate from the ion exchange resin with flowing methanol, and further flowing xylene at a temperature of the jacket of the column of 65° C. to prepare a methanol-substituted ion exchange resin column.

Three columns among the four were connected in series and the temperature of the jackets was set to 75° C. Another of the columns was used as a preliminary column. On the other hand, a polyester was prepared using zinc sorbate as catalyst and low-boiling matters were removed therefrom. The resulting polyester (zinc content: 0.2%) (one part by weight) was dissolved in xylene (5 parts by weight) to prepare a polyester-xylene solution (preparation rate: 3.6 Kg/Hr).

This polyester-xylene solution was fed at a rate of 3.6 Kg/Hr, into an extraction column being operated at 70° C., while feeding 5% hydrochloric acid at a rate of 0.1 l/Hr in counterflow to the above solution to contact the polyester-xylene solution with the 5% hydrochloric acid and thereby extract zinc sorbate into the aqueous layer, followed by further washing the resulting polyester-xylene layer with water and then feeding it into the above-mentioned ion exchange columns (three in series; jacket temperature 75° C.).

Successively, the decomposition fluid flowing out of the ion exchange resin columns was continuously cooled and filtered to separate crystals of sorbic acid and circulate the filtrate for dissolving the polyester.

Continuous operation was carried out for 240 hours under the above conditions to obtain crystals of sorbic acid (136.5 Kg, net, after correction), that is, 94.8% of the used polyester was decomposed into sorbic acid (hereinafter the weight of net crystals of sorbic acid per 100 g of the polyester will be referred to as decomposition percentage).

After lapse of the above 240 hours, the decomposition fluids at the exits of the columns were analyzed to give a decomposition percentage of 95.5%. No abnormality occurred.

The operation was further continued. As a result, while crystals of sorbic acid were quantitatively obtained, the decomposition percentage at the exit of the first column lowered since lapse of about 600 hours. Thus, the first column was separated and the above-mentioned preliminary column was connected to the last column to continue the oepration. The separated column was washed with methanol till the washing methanol became uncolored to regenerate it, followed by replacing methanol by xylene to obtain a preliminary column.

As described above, when the decomposition percentage at the first column lowers, the column is separated, a preliminary column is connected to the last column and the separated column is regenerated to prepare a preliminary column, to carry out continuous operation, and during this operation, the quantity of xylene corresponding to its loss is supplemented. As a result, operation over 6,000 hours was effected.

Comparative example 1

Example 1 was repeated except that washing with 5% hydrochloric acid was not carried out. As a result, the decomposition percentage lowered down to 85% after 120 hours; thus further operation was given up. Further, regeneration of the ion exchange resin by washing it with methanol was almost not effective.

EXAMPLE 2

Example 1 was repeated except that 5% hydrochloric acid aqueous solution used for purifying the polyesterxylene solution was replaced by 40% sulfuric acid aqueous solution. As a result, the decomposition percentage even after lapse of 4,000 hours was in the vicinity of 95%, that is, quantitative.

EXAMPLE 3

Example 1 was repeated except that the polyester (zinc content: 0.2%) was prepared using zinc acetate as catalyst and 5% hydrochloric acid water was replaced by water. The ion exchange resin used was &he same as in Example 1. As a result, even after lapse of 5,000 hours, the decomposition percentage was in the vicinity of 95% and quantitative.

EXAMPLE 4

Example 3 was repeated except that the ion exchange resin was replaced by RPC-170 (tradename of product made by Mitsubishi Kasei Co., Ltd.). As a result, even after lapse of 4,000 hours, the decomposition percentage was in the vicinity of 95%.

EXAMPLE 5

Example 2 was repeated except that the ion exchange resin was replaced by Amberlist 15 (water content: 6%) (tradename of product made by Organo Co., Ltd.), and this material was dispersed in methanol and the resulting dispersion was filled in the columns. As a result, even after 1,000 hours, the decomposition percentage was in the vicinity of 95%.

Comparative example 2

The same ion exchange resin as in Example 5 was dispersed in xylene and the resulting dispersion was filled in three columns same as in Example 5.

The same polyester (one part by weight) as in Example 1 was dissolved in xylene (3.5 parts by weight) and the solution was passed through the above columns set to a jacket temperature of 75° C. at a rate of 3.6 Kg/Hr. As a result, the decomposition percentage measured after lapse of 10 hours was in the vicinity of 93%, but that measured after lapse of 40 hours lowered down to 81%.

Thus, conc. hydrochloric acid was fed at a rate of 0.01 Kg/Hr and the temperature was raised up to 85° C., but the effect was small and the decomposition percentage lowered gradually so that the operation was stopped after lapse of 80 hours. This ion exchange resin could not be regenerated by washing with methanol, but when 5% hydrochloric acid was continuously passed through the resin to dissolve out zinc, the original catalyst performance was restored.

What is claimed is:

1. In the process for producing sorbic acid by decomposing a polyester obtained by reacting crotonaldehyde with ketene in the presence of an organic acid zinc salt, the improvement which comprises dissolving said polyester in an aromatic hydrocarbon solvent having an azeotropic temperature thereof with water of 92° to 100° C., followed by washing the resulting polyester solution with water or a mineral acid water to remove the zinc matter contained therein, and continuously contacting the resulting solution with a strongly acidic porous type ion exchange resin, said strongly acidic porous type ion exchange resin being treated with a lower alkyl alcohol in advance, followed by continuously contacting aid polyester solution with the treated resin at 60° to 95° C.

2. The improvement according to claim 1, wherein said lower alkyl alcohol is at least one member selected from the group consisting of methanol, ethanol, propanol and isopropanol.

* * * * *